(12) United States Patent
Caster et al.

(10) Patent No.: US 7,235,672 B1
(45) Date of Patent: Jun. 26, 2007

(54) PROBE, ASSAY AND KITS FOR DETECTING 11β-HYDROXYSTEROID DEHYDROGENASE AND MODULATORS THEREOF

(75) Inventors: Christopher L. Caster, San Diego, CA (US); Andrew J. Jennings, La Jolla, CA (US); Marc E. Navre, Encinitas, CA (US); Michael B. Wallace, San Diego, CA (US); Yiqin Wu, San Diego, CA (US)

(73) Assignee: Takeda San Diego, Inc., San Diego, CA (US)

( * ) Notice: Subject to any disclaimer, the term of this patent is extended or adjusted under 35 U.S.C. 154(b) by 572 days.

(21) Appl. No.: 10/800,140

(22) Filed: Mar. 11, 2004

(51) Int. Cl.
| | | |
|---|---|---|
| C07D 493/10 | (2006.01) | |
| G01N 33/532 | (2006.01) | |
| G01N 33/533 | (2006.01) | |
| G01N 33/534 | (2006.01) | |
| G01N 33/535 | (2006.01) | |
| C12Q 1/32 | (2006.01) | |

(52) U.S. Cl. .................. 549/265; 560/34; 560/39; 435/7.1; 435/7.4; 435/7.5; 435/26; 435/810; 435/975; 436/501

(58) Field of Classification Search ............... 549/265; 435/7.1, 7.4, 7.5, 26, 810, 975, 501
See application file for complete search history.

(56) References Cited

FOREIGN PATENT DOCUMENTS

JP 03-275698 A * 12/1991

\* cited by examiner

*Primary Examiner*—Bernard Dentz
(74) *Attorney, Agent, or Firm*—David J. Weitz

(57) ABSTRACT

A probe, kit comprising the probe, and methods for using the probe are provided where the probe comprises:

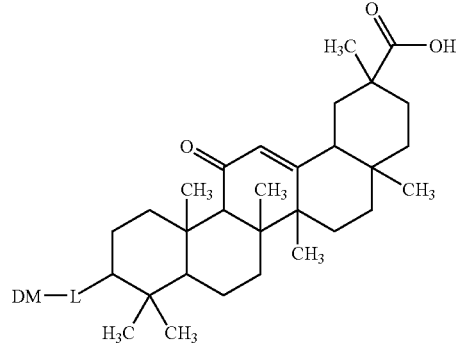

wherein
DM is a detectable marker; and
L is a straight or branched chain moiety providing between 1 and 20 atom separation between DM and the ring atom to which DM is attached.

63 Claims, 2 Drawing Sheets

FIGURE 1

Amino acid sequence for full-length human wild type HSD11B1 [SEQ. ID No. 1]
(Residues 24-292 are underlined)

```
  1 MAFMKKYLLP ILGLFMAYYY YSANEEFRPE MLQGKKVIVT GASKGIGREM AYHLAKMGAH
 61 VVVTARSKET LQKVVSHCLE LGAASAHYIA GTMEDMTFAE QFVAQAGKLM GGLDMLILNH
121 ITNTSLNLFH DDIHHVRKSM EVNFLSYVVL TVAALPMLKQ SNGSIVVVSS LAGKVAYPMV
181 AAYSASKFAL DGFFSSIRKE YSVSRVNVSI TLCVLGLIDT ETAMKAVSGI VHMQAAPKEE
241 CALEIIKGGA LRQEEVYYDS SLWTTLLIRN PCRKILEFLY STSYNMDRFI NK
```

Amino acid sequence for residues 24-292 of HSB11B1 with a
N-terminal MKHQHQHQHQHQHQQPL tag [SEQ. ID No. 2]
(N-terminal MKHQHQHQHQHQHQQPL tag is underlined)

```
  1 MKHQHQHQHQ HQHQQPLNEE FRPEMLQGKK VIVTGASKGI GREMAYHLAK MGAHVVVTAR
 61 SKETLQKVVS HCLELGAASA HYIAGTMEDM TFAEQFVAQA GKLMGGLDML ILNHITNTSL
121 NLFHDDIHHV RKSMEVNFLS YVVLTVAALP MLKQSNGSIV VVSSLAGKVA YPMVAAYSAS
181 KFALDGFFSS IRKEYSVSRV NVSITLCVLG LIDTETAMKA VSGIVHMQAA PKEECALEII
241 KGGALRQEEV YYDSSLWTTL LIRNPCRKIL EFLYSTSYNM DRFINK
```

Human cDNA sequence encoding residues 24-292 of HSD11B1 [SEQ. ID No. 3]

```
   1 ACAATTCAGA GGCTGCTGCC TGCTTAGGAG GTTGTAGAAA GCTCTGTAGG TTCTCTCTGT
  61 GTGTCCTACA GGAGTCTTCA GGCCAGCTCC CTGTCGGATG GCTTTTATGA AAAAATATCT
 121 CCTCCCCATT CTGGGGCTCT TCATGGCCTA CTACTACTAT TCTGCAAACG AGGAATTCAG
 181 ACCAGAGATG CTCCAAGGAA AGAAAGTGAT TGTCACAGGG GCCAGCAAAG GGATCGGAAG
 241 AGAGATGGCT TATCATCTGG CGAAGATGGG AGCCCATGTG GTGGTGACAG CGAGGTCAAA
 301 AGAAACTCTA CAGAAGGTGG TATCCCACTG CCTGGAGCTT GGAGCAGCCT CAGCACACTA
 361 CATTGCTGGC ACCATGGAAG ACATGACCTT CGCAGAGCAA TTTGTTGCCC AAGCAGGAAA
 421 GCTCATGGGA GGACTAGACA TGCTCATTCT CAACCACATC ACCAACACTT CTTTGAATCT
 481 TTTTCATGAT GATATTCACC ATGTGCGCAA AAGCATGGAA GTCAACTTCC TCAGTTACGT
 541 GGTCCTGACT GTAGCTGCCT TGCCCATGCT GAAGCAGAGC AATGGAAGCA TTGTTGTCGT
 601 CTCCTCTCTG GCTGGGAAAG TGGCTTATCC AATGGTTGCT GCCTATTCTG CAAGCAAGTT
 661 TGCTTTGGAT GGGTTCTTCT CCTCCATCAG AAAGGAATAT TCAGTGTCCA GGGTCAATGT
 721 ATCAATCACT CTCTGTGTTC TTGGCCTCAT AGACACAGAA ACAGCCATGA AGGCAGTTTC
 781 TGGGATAGTC CATATGCAAG CAGCTCCAAA GGAGGAATGT GCCCTGGAGA TCATCAAAGG
 841 GGGAGCTCTG CGCCAAGAAG AAGTGTATTA TGACAGCTCA CTCTGGACCA CTCTTCTGAT
 901 CAGAAATCCA TGCAGGAAGA TCCTGGAATT TCTCTACTCA ACGAGCTATA ATATGGACAG
 961 ATTCATAAAC AAGTAGGAAC TCCCTGAGGG CTGGGCATGC TGAGGGATTT TGGGACTGTT
1021 CTGTCTCATG TTTATCTGAG CTCTTATCTA TGAAGACATC TTCCCAGAGT GTCCCCAGAG
1081 ACATGCAAGT CATGGGTCAC ACCTGACAAA TGGAAGGAGT CCTCTAACA TTTGCAAAAT
1141 GGAAATGTAA TAATAATGAA TGTCATGCAC CGCTGCAGCC AGCAGTTGTA AAATTGTTAG
1201 TAAACATAGG TATAATTACC AGATAGTTAT ATTAAATTTA TATCTTATAT ATAATAATAT
1261 GTGATGATTA ATACAATATT AATTATAATA AAGGTCACAT AAACTTTATA AATTCATAAC
1321 TGGTAGCTAT AACTTGAGCT TATTCAGGAT GGTTTCTTTA AAACCATAAA CTGTACAAAT
1381 GAAATTTTTC AATATTTGTT    TCTTA
```

FIGURE 1 (Cont.)

DNA sequence encoding PCR Primer hsd1_24-f [SEQ. ID No. 4]

1 AACGAGGAAT TCAGACCAGA GATG

DNA sequence encoding PCR Primer hsd1-292-r [SEQ. ID No. 5]

1 TTACTTGTTT ATGAATCTGT CCAT

DNA sequence encoding PCR Primer hsdC272Sqcf [SEQ. ID No. 6]

1 TCAGAAATCC ATCCAGGAAG ATC

DNA sequence encoding PCR Primer hsdC272Sqcr [SEQ. ID No. 7]

1 GATCTTCCTG GATGGATTTC TGA

SEQUENCE LISTING

<160> NUMBER OF SEQ ID NOS: 7

<210> SEQ ID NO 1
<211> LENGTH: 292
<212> TYPE: PRT
<213> ORGANISM: Homo sapiens
<220> FEATURE:

```
<221> NAME/KEY: MISC_FEATURE
<222> LOCATION: (1)..(292)
<223> OTHER INFORMATION: Amino acid sequence for full-length human wild
      type 11B-hydroxysteroid dehydrogenase

<400> SEQUENCE: 1

Met Ala Phe Met Lys Lys Tyr Leu Leu Pro Ile Leu Gly Leu Phe Met
1               5                   10                  15

Ala Tyr Tyr Tyr Ser Ala Asn Glu Glu Phe Arg Pro Glu Met Leu
            20                  25                  30

Gln Gly Lys Lys Val Ile Val Thr Gly Ala Ser Lys Gly Ile Gly Arg
        35                  40                  45

Glu Met Ala Tyr His Leu Ala Lys Met Gly Ala His Val Val Val Thr
50                  55                  60

Ala Arg Ser Lys Glu Thr Leu Gln Lys Val Val Ser His Cys Leu Glu
65                  70                  75                  80

Leu Gly Ala Ala Ser Ala His Tyr Ile Ala Gly Thr Met Glu Asp Met
                85                  90                  95

Thr Phe Ala Glu Gln Phe Val Ala Gln Ala Gly Lys Leu Met Gly Gly
                100                 105                 110

Leu Asp Met Leu Ile Leu Asn His Ile Thr Asn Thr Ser Leu Asn Leu
            115                 120                 125

Phe His Asp Asp Ile His His Val Arg Lys Ser Met Glu Val Asn Phe
        130                 135                 140

Leu Ser Tyr Val Val Leu Thr Val Ala Ala Leu Pro Met Leu Lys Gln
145                 150                 155                 160

Ser Asn Gly Ser Ile Val Val Ser Ser Leu Ala Gly Lys Val Ala
                165                 170                 175

Tyr Pro Met Val Ala Ala Tyr Ser Ala Ser Lys Phe Ala Leu Asp Gly
            180                 185                 190

Phe Phe Ser Ser Ile Arg Lys Glu Tyr Ser Val Ser Arg Val Asn Val
        195                 200                 205

Ser Ile Thr Leu Cys Val Leu Gly Leu Ile Asp Thr Glu Thr Ala Met
210                 215                 220

Lys Ala Val Ser Gly Ile Val His Met Gln Ala Ala Pro Lys Glu Glu
225                 230                 235                 240

Cys Ala Leu Glu Ile Ile Lys Gly Gly Ala Leu Arg Gln Glu Glu Val
                245                 250                 255

Tyr Tyr Asp Ser Ser Leu Trp Thr Thr Leu Leu Ile Arg Asn Pro Cys
            260                 265                 270

Arg Lys Ile Leu Glu Phe Leu Tyr Ser Thr Ser Tyr Asn Met Asp Arg
        275                 280                 285

Phe Ile Asn Lys
    290

<210> SEQ ID NO 2
<211> LENGTH: 286
<212> TYPE: PRT
<213> ORGANISM: Artificial
<220> FEATURE:
<223> OTHER INFORMATION: Amino acid sequence for residues 24-292 of
      11B-hydroxysteroid dehydrogenase with a N-terminal
      MKHQHQHQHQHQQPL tag

<400> SEQUENCE: 2

Met Lys His Gln His Gln His Gln His Gln His Gln Gln Pro
1               5                   10                  15
```

```
Leu Asn Glu Glu Phe Arg Pro Glu Met Leu Gln Gly Lys Lys Val Ile
             20                  25                  30

Val Thr Gly Ala Ser Lys Gly Ile Gly Arg Glu Met Ala Tyr His Leu
         35                  40                  45

Ala Lys Met Gly Ala His Val Val Thr Ala Arg Ser Lys Glu Thr
 50                  55                  60

Leu Gln Lys Val Val Ser His Cys Leu Glu Leu Gly Ala Ala Ser Ala
 65                  70                  75                  80

His Tyr Ile Ala Gly Thr Met Glu Asp Met Thr Phe Ala Glu Gln Phe
                 85                  90                  95

Val Ala Gln Ala Gly Lys Leu Met Gly Gly Leu Asp Met Leu Ile Leu
            100                 105                 110

Asn His Ile Thr Asn Thr Ser Leu Asn Leu Phe His Asp Asp Ile His
            115                 120                 125

His Val Arg Lys Ser Met Glu Val Asn Phe Leu Ser Tyr Val Val Leu
130                 135                 140

Thr Val Ala Ala Leu Pro Met Leu Lys Gln Ser Asn Gly Ser Ile Val
145                 150                 155                 160

Val Val Ser Ser Leu Ala Gly Lys Val Ala Tyr Pro Met Val Ala Ala
                165                 170                 175

Tyr Ser Ala Ser Lys Phe Ala Leu Asp Gly Phe Phe Ser Ser Ile Arg
            180                 185                 190

Lys Glu Tyr Ser Val Ser Arg Val Asn Val Ser Ile Thr Leu Cys Val
            195                 200                 205

Leu Gly Leu Ile Asp Thr Glu Thr Ala Met Lys Ala Val Ser Gly Ile
210                 215                 220

Val His Met Gln Ala Ala Pro Lys Glu Glu Cys Ala Leu Glu Ile Ile
225                 230                 235                 240

Lys Gly Gly Ala Leu Arg Gln Glu Glu Val Tyr Tyr Asp Ser Ser Leu
                245                 250                 255

Trp Thr Thr Leu Leu Ile Arg Asn Pro Cys Arg Lys Ile Leu Glu Phe
            260                 265                 270

Leu Tyr Ser Thr Ser Tyr Asn Met Asp Arg Phe Ile Asn Lys
            275                 280                 285

<210> SEQ ID NO 3
<211> LENGTH: 1405
<212> TYPE: DNA
<213> ORGANISM: Artificial
<220> FEATURE:
<223> OTHER INFORMATION: Human cDNA sequence encoding residues 24-292 of
      11B-hydroxysteroid dehydrogenase

<400> SEQUENCE: 3
acaattcaga ggctgctgcc tgcttaggag gttgtagaaa gctctgtagg ttctctctgt      60
gtgtcctaca ggagtcttca ggccagctcc ctgtcggatg gcttttatga aaaaatatct    120
cctccccatt ctggggctct tcatggccta ctactactat tctgcaaacg aggaattcag    180
accagagatg ctccaaggaa agaaagtgat tgtcacaggg gccagcaaag ggatcggaag    240
agagatggct tatcatctgg cgaagatggg agcccatgtg gtggtgacag cgaggtcaaa    300
agaaactcta cagaaggtgg tatcccactg cctggagctt ggagcagcct cagcacacta    360
cattgctggc accatggaag acatgacctt cgcagagcaa tttgttgccc aagcaggaaa    420
gctcatggga ggactagaca tgctcattct caaccacatc accaacactt ctttgaatct    480
ttttcatgat gatattcacc atgtgcgcaa aagcatggaa gtcaacttcc tcagttacgt    540
```

```
ggtcctgact gtagctgcct tgcccatgct gaagcagagc aatggaagca ttgttgtcgt    600
ctcctctctg gctgggaaag tggcttatcc aatggttgct gcctattctg caagcaagtt    660
tgctttggat gggttcttct cctccatcag aaaggaatat tcagtgtcca gggtcaatgt    720
atcaatcact ctctgtgttc ttggcctcat agacacagaa acagccatga aggcagtttc    780
tgggatagtc catatgcaag cagctccaaa ggaggaatgt gccctggaga tcatcaaagg    840
gggagctctg cgccaagaag aagtgtatta tgacagctca ctctggacca ctcttctgat    900
cagaaatcca tgcaggaaga tcctggaatt tctctactca acgagctata atatggacag    960
attcataaac aagtaggaac tccctgaggg ctgggcatgc tgagggattt tgggactgtt   1020
ctgtctcatg tttatctgag ctcttatcta tgaagacatc ttcccagagt gtccccagag   1080
acatgcaagt catgggtcac acctgacaaa tggaaggagt tcctctaaca tttgcaaaat   1140
ggaaatgtaa taataatgaa tgtcatgcac cgctgcagcc agcagttgta aaattgttag   1200
taaacatagg tataattacc agatagttat attaaattta tatcttatat ataataatat   1260
gtgatgatta atacaatatt aattataata aggtcacat aaactttata aattcataac    1320
tggtagctat aacttgagct tattcaggat ggtttcttta aaaccataaa ctgtacaaat   1380 gaaattttc aatatttgtt tctta                                          1405
```

<210> SEQ ID NO 4
<211> LENGTH: 24
<212> TYPE: DNA
<213> ORGANISM: Artificial
<220> FEATURE:
<223> OTHER INFORMATION: DNA sequence encoding PCR primer hsd1_24-f

<400> SEQUENCE: 4

```
aacgaggaat tcagaccaga gatg                                            24
```

<210> SEQ ID NO 5
<211> LENGTH: 24
<212> TYPE: DNA
<213> ORGANISM: Artificial
<220> FEATURE:
<223> OTHER INFORMATION: DNA sequence encoding PCR primer hsd1_292-r

<400> SEQUENCE: 5

```
ttacttgttt atgaatctgt ccat                                            24
```

<210> SEQ ID NO 6
<211> LENGTH: 23
<212> TYPE: DNA
<213> ORGANISM: Artificial
<220> FEATURE:
<223> OTHER INFORMATION: DNA sequence encoding PCR primer hsdC272Sqcf

<400> SEQUENCE: 6

```
tcagaaatcc atccaggaag atc                                             23
```

<210> SEQ ID NO 7
<211> LENGTH: 23
<212> TYPE: DNA
<213> ORGANISM: Artificial
<220> FEATURE:
<223> OTHER INFORMATION: DNA sequence encoding PCR primer hsdC272Sqcr

<400> SEQUENCE: 7

```
gatcttcctg gatggatttc tga                                             23
```

PROBE, ASSAY AND KITS FOR DETECTING 11β-HYDROXYSTEROID DEHYDROGENASE AND MODULATORS THEREOF

FIELD OF THE INVENTION

The invention relates to a probe and assays using that probe for detecting 11β-hydroxysteroid dehydrogenase type 1.

DESCRIPTION OF RELATED ART

A wide variety of assays are known in the art for detecting the presence or absence of a particular protein in a sample. Assays are also known in the art for identifying protein modulators that are capable of binding to a particular protein. These assays generally depend upon the use of a probe that specifically binds to a particular protein or a particular class of proteins.

In addition to qualitatively detecting the presence or absence of a particular protein or protein modulator in a sample, assays may also be used quantitatively. For example, assays may be used to quantify an amount of a particular protein in a sample. Assays may also be used to quantify the amount of a protein modulator present in a sample and may be used to quantify a physical property of the protein modulator, such as the protein modulator's binding affinity for the particular protein.

11β-hydroxysteroid dehydrogenase type 1 (HSD11B1) is a member of the short chain dehydrogenase subfamily. HSD11B1 is a microsomal enzyme that catalyzes the conversion of the stress hormone cortisol to the inactive metabolite cortisone. In addition, the protein can catalyze the reverse reaction, the conversion of cortisone to cortisol. HSD11B1 is important in regulating local concentrations of glucocorticoids in various tissue types, including adipose, liver, vascular, brain, testis, ocular and placental tissues. Disregulation of HSD11B1 is implicated in such areas as metabolic syndromes (e.g., diabetes and obesity), Cushing's disease, hypertension, cognitive function (e.g., dementia), ocular function (e.g., intraocular pressure), and osteoporosis.

Researchers are interested in developing drugs directed to HSD11B1. In support of such research, a need exists for assays that may be used to detect HSD11B1 as well as potential protein modulators for HSD11B1.

SUMMARY OF THE INVENTION

In one of its aspects, the present invention relates to probes comprising:

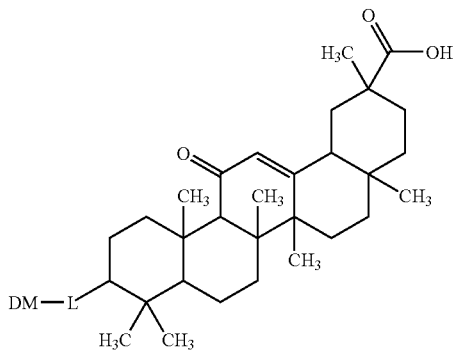

wherein
DM is a detectable marker; and
L is a straight or branched chain moiety providing between 1 and 20 atom separation between DM and the ring atom to which DM is attached.

In one variation, the probe has the general formula:

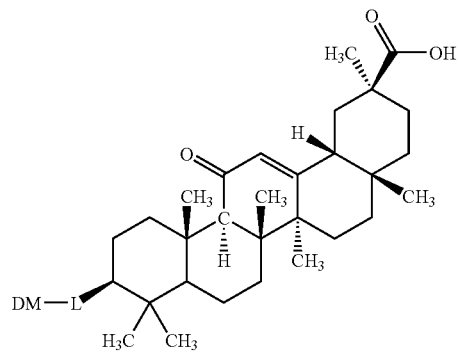

Generally, L, also referred to herein as a "linker," may be any moiety that covalently connects the detectable marker to the remainder of the probe. In relation to the above embodiment, L may optionally comprise the formula:

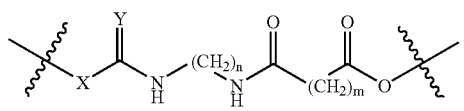

where X is NH or a single bond; Y is S or O; m is $\geq 2$; and n is $\geq 2$. In one variation, X is NH and Y is S. In another variation, m is 2 or 3 and n is 2, 3, 4, 5, or 6.

DM, also referred to herein as a "detectable marker," may be any moiety that allows for detection of the probe, whether directly or indirectly. Examples of types of detectable markers include but are not limited to members of the group consisting of photoreactive groups; fluorescent labels; chemiluminescent labels; colorimeteric labels; enzymatic markers; radioactive isotopes; biotin-streptavidin; digoxigenin haptens; and electron-dense reagents.

In a particular variation, DM comprises the formula:

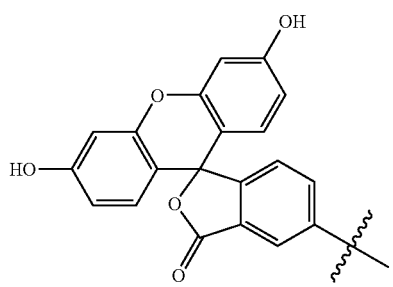

It is noted in regard to each of the probes of the present invention that the probes may optionally be attached to a solid support.

A variety of methods are also provided for using the probes of the present invention. In regard to these methods, the term "target protein" refers to a particular protein that is involved in the assay method employing a probe according to the present invention. The term "protein modulator" or "modulator of a protein" refers to any compound or other entity that is capable of binding to a particular target protein. The term "test compound" refers to a compound to be tested regarding whether it is a protein modulator of a particular target protein.

In one embodiment, a method is provided that comprises contacting a probe according to the present invention with a target protein to which the probe is capable of binding; and detecting the probe. This method may be used, for example, to detect a target protein in a sample and may also be used to quantify an amount of target protein in a sample. As will be described herein, the method may also be used to evaluate test compounds as protein modulators of the target protein.

In addition to detecting the probe itself, detecting the probe may optionally include detecting a probe—target protein complex. In this regard, the probe may be designed so that the detectable marker allows one to differentiate between free, unbound probe and probe bound to a target protein. This probe design allows for the detection of a probe—target protein complex without having to isolate either the probe or the target protein. It also allows one to conduct the method where the probe and the target protein are both in solution. In one variation, the detectable marker is a fluorescent label. This allows one to detect the probe by fluorescence polarization, a method that is able to distinguish free, unbound probe and probe bound to a target protein.

The target protein may also optionally be attached to a solid support. This allows the solid support to be washed in order to remove probe that is not bound to the solid support via the target protein prior to detecting the probe.

The present invention also relates to a method comprising: contacting a target protein with one or more test compounds in the presence of a probe according to the present invention; and detecting the probe. It is noted that test compounds may be added to a sample comprising the target protein before, after or at the same time as the test protein and/or the probe, depending on the design of the method.

As noted above, detecting the probe may include detecting a probe—target protein complex. For example, in one variation, the method comprises: contacting a probe according to the present invention with a target protein to which the probe is capable of binding in the absence of test compounds; detecting a formation of a probe—target protein complex; adding one or more test compounds; and detecting a change in the amount of probe—target protein complex after addition of the one or more test compounds. Detection of the probe—target protein complex and the change in the amount of probe—target protein complex after addition of the one or more test compounds may optionally be performed by fluorescence polarization.

The method may be conducted such that the probe, target protein and test compounds are all in solution. The method may also be conducted such that the target protein is attached to a solid support.

The above method may be used in relation to screening a plurality of test compounds for their ability to bind to the target protein. In this regard, it may be desirable to screen such test compounds in a high throughput manner, for example by using a multiwell plate or by attaching the test protein to a solid support. The above method may also be used to evaluate test compounds for their properties as protein modulators. For example, the probes of the present invention may be used to determine the binding affinity of a given test compound for the target protein.

Each of the above embodiments may include performing one or more control experiments where no test compounds are added and/or no target protein is added. This allows results from detecting the probe with and without test compounds and/or target proteins being present to be compared. One or more control experiments may also be performed in order to form a standard curve against which particular experiments can be measured.

In regard to each of the above method embodiments, how the probe is detected is dependent upon the type of detectable marker employed. Detection may be achieved by direct or indirect detection of the detectable marker.

Detection of the detectable marker may indicate the presence of the probe. Detection may also be conducted so that detection of the detectable marker indicates the presence of a probe—target protein complex.

In instances where the detectable marker is fluorescent, detection of the detectable marker may include detecting a fluorescent signal from the detectable marker. Fluorescence polarization may also be used to detect a probe—target protein complex.

In instances where the detectable marker is visible, detection of the detectable marker may include visible detection of the detectable marker. In instances where the detectable marker is a substrate for an enzymatic reaction, detection of the detectable marker may first include having the detectable marker undergo the enzymatic reaction, followed by detection of the enzyme reaction product.

In each of the above embodiments, the methods may optionally be conducted in a high throughput format. Various high throughput formats are known in the art and may be used herein. For example, a plurality of separate experiments may be conducted in wells of a multiwell plate. If the target protein is attached to a solid support, separate regions of the solid support may be defined, each for conducting a separate experiment.

Also in regard to each of the above embodiments, the methods may optionally include one or more washing steps as necessary or desirable to remove unbound probe, target protein, and/or test compounds prior to detection of the probe.

The probes of the present invention have the property of being able to bind to 11β-hydroxysteroid dehydrogenase type 1 and as such are useful in methods involving 11β-hydroxysteroid dehydrogenase type 1. Accordingly, all of methods of the present invention may be conducted where the target protein is 11β-hydroxysteroid dehydrogenase type 1. It is noted that the probes of the present invention may also be used in relation to proteins other than 11β-hydroxysteroid dehydrogenase type 1 to which the probes of the present invention also bind, whether in a covalent or non-covalent manner.

Also provided are compositions and articles of manufacture incorporating the probes of the present invention which may be used, among other things, for practicing the methods of the present invention. In one embodiment, a composition is provided comprising a probe according to the present invention and a target protein, particularly HSD11B1. The composition may be as a powder ready for reconstitution and use in an assay. Alternatively, the composition may be an aqueous solution comprising the probe and the target protein. In another embodiment, a composition is provided comprising a probe according to the present invention attached to a solid support. The probes and compositions of the present invention may be provided as part of a kit as described herein.

The present invention also provides kits incorporating the probes of the present invention which may be used, among other things, for practicing the methods of the present invention.

In one embodiment, a kit is provided that comprises a probe according to the present invention. The kit may optionally include a protein to which the probe is capable of binding. In one variation, the protein is 11β-hydroxysteroid dehydrogenase type 1. The kit may also include one or more known protein modulators that may be used as a standard in conjunction with the probe. Within the kit, the probe, protein, and/or protein modulator(s) may each independently be (a) in purified form; (b) attached to a solid support; and/or (c) in solution, depending on the design of assay for which the kit is designed.

The kit may also comprise instructions for using the probe or for storing the probe and kit. The kit may also comprise packaging materials for housing one or more compositions comprising the probe, protein, and/or protein modulator(s). Examples of packaging materials include, but are not limited to containers or compartments that are used to house the probe, protein, and/or protein modulator(s). The packaging materials may include written information including instructions regarding the probe and the kit. Other elements typically incorporated in kits used in biological assays may also be included.

BRIEF DESCRIPTION OF THE FIGURES

FIG. 1 illustrates SEQ. ID Nos. 1, 2, 3, 4, 5, 6, and 7 referred to in this application.

DETAILED DESCRIPTION OF THE INVENTION

The present invention relates to assays for detecting a protein, methods for identifying compounds that bind to the protein, and probes useful therefor. In particular, the invention relates to assays for detecting 11β-hydroxysteroid dehydrogenase type 1, methods for identifying compounds that bind to 11β-hydroxysteroid dehydrogenase type 1, and probes useful therefor.

1. Probes

In one of its aspects, the present invention relates to probes having the formula:

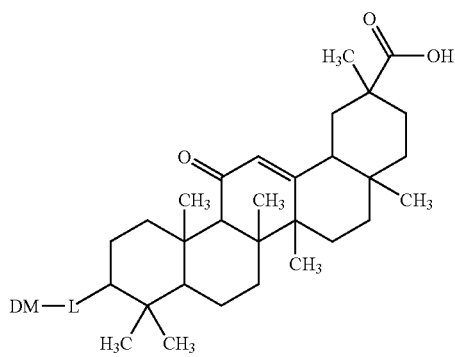

wherein
DM is a detectable marker; and
L is a straight or branched chain moiety providing between 1 and 20 atom separation between DM and the ring atom to which DM is attached.

In one variation, the probe has the general formula:

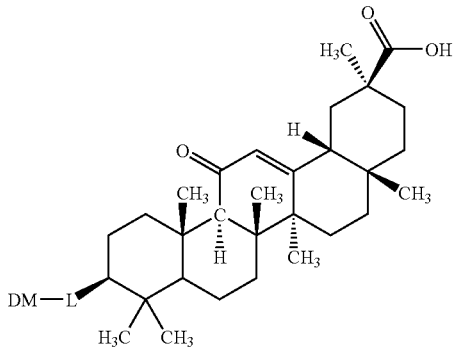

It is also noted that the probes of the present invention, unless otherwise specifically specified, are intended to cover the chemical entity itself, as well as all ionized forms (e.g., salts) and solvates (e.g., hydrates), all possible stereoisomers, and all possible resonance forms and tautomers.

It should be recognized that the probes of the present invention may be present and optionally used in the form of salts and/or hydrates. For example, it is within the scope of the present invention to convert the probes of the present invention into, and use them in the form of, their salts derived from various organic and inorganic acids and bases in accordance with procedures well known in the art. Probes of the present invention may also be conveniently prepared, or formed during the process of the invention, as solvates (e.g., hydrates). Hydrates of probes of the present invention may be conveniently prepared by recrystallization from an aqueous/organic solvent mixture, using organic solvents such as dioxane, tetrahydrofuran or methanol.

It is also noted that unless a particular stereochemistry is specified, recitation of a probe is intended to encompass all possible stereoisomers (e.g., enantiomers or diastereomers depending on the number of chiral centers), independent of whether the probe is present as an individual isomer or a mixture of isomers. Further, unless otherwise specified, recitation of a probe is intended to encompass all possible resonance forms and tautomers. With regard to the claims, the language "probe comprising the formula" is intended to encompass the probe and all ionized forms and solvates, all possible stereoisomers, and all possible resonance forms and tautomers unless otherwise specifically specified in the particular claim.

A. Detectable Markers (DM)

DM, also referred to herein as a "detectable marker," may be any moiety that allows for detection of the probe, whether directly (where the detectable marker comprises a moiety that is detected directly or that produces a directly detectable moiety) or indirectly (where the detected marker binds to a primary detectable marker, e.g., as is common in immunological labeling).

Review articles describing detectable markers that may be used herein and methods for detecting detectable markers include Polak and Van Noorden, *Introduction to Immunocytochemistry*, 2nd ed., Springer Verlag, NY (1997); and Haugland, *Handbook of Fluorescent Probes and Research Chemicals*, a combined handbook and catalogue, Molecular Probes, Inc., OR (1996).

Examples of types of detectable markers that may be employed include, but are not limited to, members of the group consisting of photoreactive groups; fluorescent labels; chemiluminescent labels; colorimeteric labels; enzymatic markers; radioactive isotopes; biotin-streptavidin; digoxigenin haptens; and electron-dense reagents. It is noted that detectable markers can comprise undetected subcomponents as well as detected subcomponents.

More particular examples of detectable markers that may be used in the present invention include spectroscopically detectable labels such as fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.)); chemiluminescent dyes (e.g., digoxigenin, biotin, phycoerythrin, AMCA, CyDyes™, and the like); radiolabels (e.g., $^3$H, $^{125}$I, $^{35}$S, $^{14}$C, $^{32}$P, $^{33}$P, etc.); enzymes (e.g., horse radish peroxidase, alkaline phosphatase, etc.); spectral calorimetric labels such as colloidal gold or colored glass or plastic (e.g., polystyrene, polypropylene, latex, etc.) beads; and photoreactive groups (e.g., benzophenones, azides, and other moieties that transform upon activation by light).

The detectable marker may also be an enzyme substrate where the product of an enzyme reaction is detected. Examples of suitable enzymes include but are not limited to β-galactosidase, luciferase, and horse radish peroxidase. An example of a chemiluminescent substrate for luciferase is luciferin. An example of a chemiluminescent substrate for β-galactosidase is 4-methylumbelliferyl-β-D-galactoside. Examples of chemiluminescent substrates for alkaline phosphatase substrates include p-nitrophenyl phosphate (pNPP), which is typically detected with a spectrophotometer; 5-bromo-4-chloro-3-indolyl phosphate/nitro blue tetrazolium (BCIP/NBT) and fast red/napthol AS-TR phosphate, which may be detected visually; and 4-methoxy-4-(3-phosphonophenyl) spiro[1,2-dioxetane-3,2'-adamantane], which may be detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which may be detected with a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4C1N), which may be detected visually. Other enzyme substrates that may be used as detectable markers are known to those skilled in the art. Enzyme-substrate reactions and product detection may be performed according to standard procedures known to those skilled in the art and kits for performing enzyme immunoassays are available.

B. Linkers (L)

L, also referred to herein as a "linker," may be any moiety that covalently connects the detectable marker to the remainder of the probe.

Particular examples of linkers that may be used include, but are not limited to, amino acid residues, poly(ethylene glycol) linkages (Shearwater Polymers, Inc., Huntsville, Ala.), and moieties derived therefrom. For example, linkers can be derived from glycine, β-alanine, aminopentanoic acid, aminohexanoic acid, aminohepanoic acid, aminooctanoic acid, aminononanoic acid, aminodecanoic acid, aminoundecanoic acid, and aminododecanoic acid. The linker may optionally comprise amide, sulfhydryl, and/or heterofunctional linkages. Since each of these moieties include an amino and a carboxylic acid functionality, each may be incorporated into the probe using a peptide bond.

The below formula provides a particular example of a linker that may be used in the present invention:

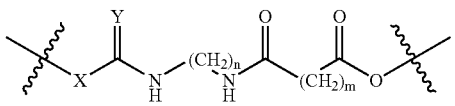

where X is NH or a single bond; Y is S or O; m is $\geq 2$; and n is $\geq 2$. In one variation, X is NH and Y is S. In another variation, m is 2 or 3 and n is 2, 3, 4, 5, or 6.

C. Preparation of Probes

Probes according to the present invention may be synthesized according to a variety of reaction schemes. Some illustrative schemes are provided herein. Other reaction schemes could be readily devised by those skilled in the art.

The symbols and conventions used in the processes, schemes and examples described herein are intended to be consistent with those used in the contemporary scientific literature, for example, the Journal of the American Chemical Society or the Journal of Biological Chemistry. Standard single-letter or thee-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| g (grams); | mg (milligrams); |
| L (liters); | mL (milliliters); |
| μL (microliters); | psi (pounds per square inch); |
| M (molar); | mM (millimolar); |
| i.v. (intravenous); | Hz (Hertz); |
| MHz (megahertz); | mol (moles); |
| mmol (millimoles); | RT (ambient temperature); |
| min (minutes); | h (hours); |
| mp (melting point); | TLC (thin layer chromatography); |
| Tr (retention time); | RP (reverse phase); |
| MeOH (methanol); | i-PrOH (isopropanol); |
| TEA (triethylamine); | TFA (trifluoroacetic acid); |
| TFAA (trifluoroacetic anhydride); | THF (tetrahydrofuran); |
| DMSO (dimethylsulfoxide); | EtOAc (ethyl acetate); |
| DME (1,2-dimethoxyethane); | DCM (dichloromethane); |
| DCE (dichloroethane); | DMF (N,N-dimethylformamide); |
| DMPU (N,N'-dimethyl-propyleneurea); | CDI (1,1-carbonyldiimidazole); |
| IBCF (isobutyl chloroformate); | HOAc (acetic acid); |
| HOSu (N-hydroxysuccinimide); | HOBT (1-hydroxybenzotriazole); |
| Et$_2$O (diethyl ether); | EDCI (ethylcarbodiimide hydrochloride); |
| BOC (tert-butyloxycarbonyl); | FMOC (9-fluorenylmethoxy-carbonyl); |
| DCC (dicyclohexylcarbodiimide); | CBZ (benzyloxycarbonyl); |
| Ac (acetyl); | atm (atmosphere); |
| TMSE (2-(trimethylsilyl)ethyl); | TMS (trimethylsilyl); |
| TIPS (triisopropylsilyl); | TBS (t-butyldimethylsilyl); |
| DMAP (4-dimethylaminopyridine); | Me (methyl); |
| OMe (methoxy); | Et (ethyl); |
| Et (ethyl); | tBu (tert-butyl); |
| HPLC (high pressure liquid chomatography); | |
| BOP (bis(2-oxo-3-oxazolidinyl)-phosphinic chloride); | |
| TBAF (tetra-n-butylammonium fluoride); and | |
| mCPBA (meta-chloroperbenzoic acid). | |

All references to ether or Et$_2$O are to diethyl ether; brine refers to a saturated aqueous solution of NaCl. Unless otherwise indicated, all temperatures are expressed in ° C. (degrees Centigrade). All reactions conducted under an inert atmosphere at RT unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60F-254), visualized with UV light, 5% ethanolic phosphomolybdic acid, Ninhydrin or p-anisaldehyde solution. Flash column chromatography was performed on silica gel (230–400 mesh, Merck).

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Probes according to the present invention wherein X is NH and Y is S may optionally be synthesized according to the following general reaction scheme (Scheme I):

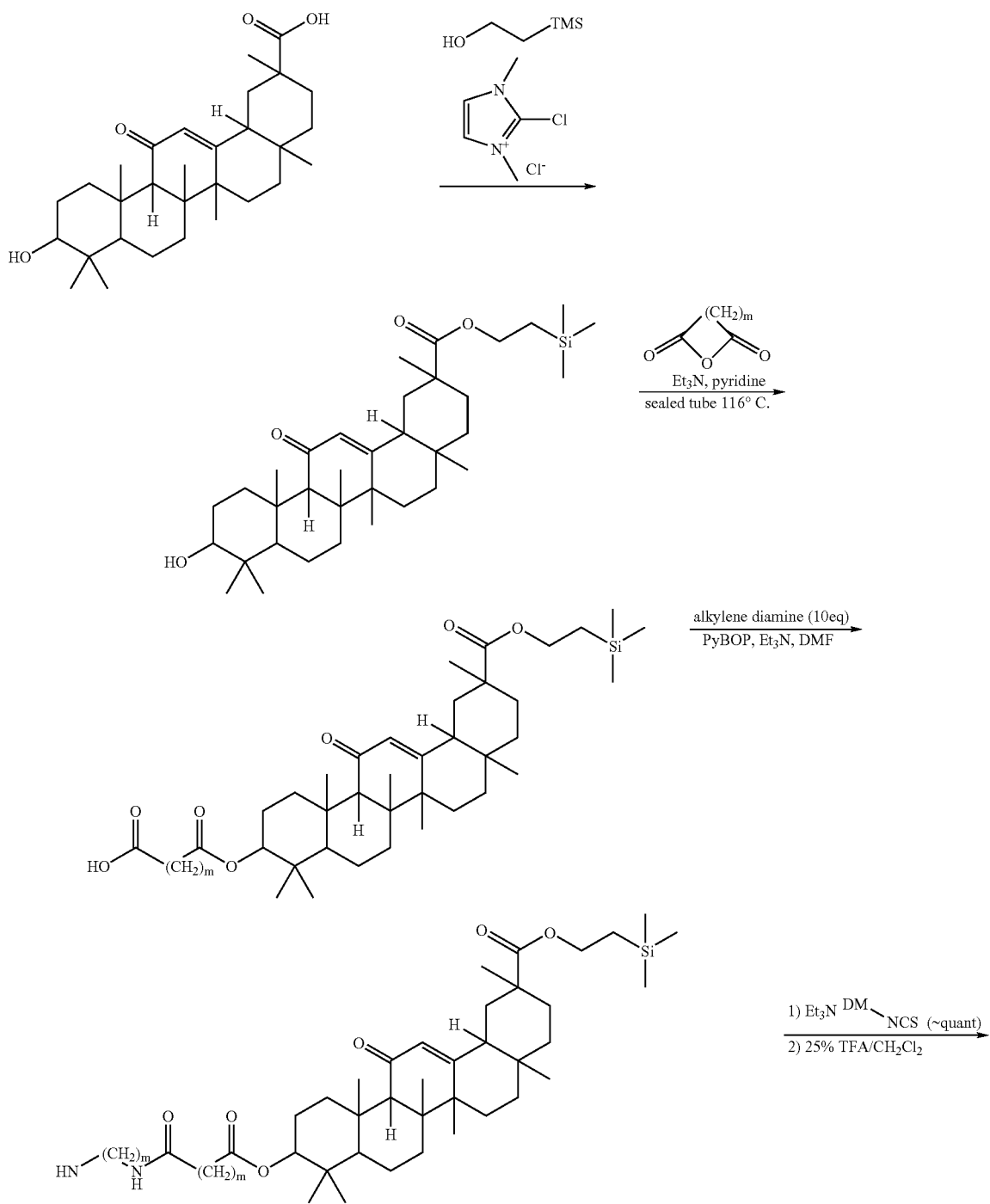

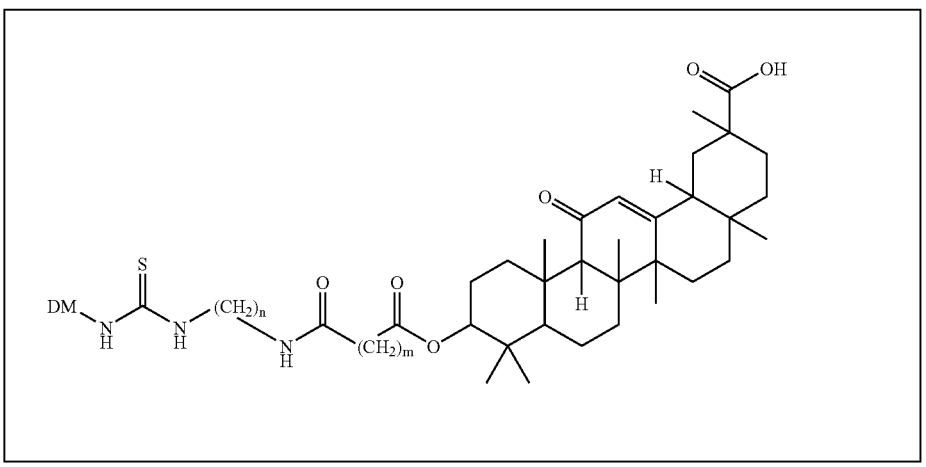

wherein m is ≧2, and preferably 2 or 3; n is ≧2, and preferably 2, 3, 4, 5, or 6; and DM is a detectable marker as described herein. In brief, a solution of 18-β-glycyrrhetic acid in pyridine is reacted with 2-(Trimethylsilyl)ethanol and 2-chloro-1,3-dimethylimidazolinium chloride. The reaction mixture is then poured over water and extracted with $CH_2Cl_2$. The organics are optionally washed, dried, and concentrated, and purified to yield 18-β-Glycyrrhetic acid 2-trimethylsilanyl-ethyl ester. The 18-β-Glycyrrhetic acid 2-trimethylsilanyl-ethyl ester product is then combined with an anhydride in pyridine with triethylamine, and the solution is heated. The reaction mixture is then cooled and concentrated. The residue is diluted with acetone and ice water, and the pH adjusted to about pH=3. The solution is then extracted with EtOAc, and the organics were dried, concentrated, and purified to yield 18-(Carboxyalkylcarbonyloxy)-18-β-glycyrrhetic acid 2-trimethylsilanyl-ethyl ester. The product is stirred with alkylenediamine in DMF, and PyBOP and triethylamine are added. The solution is then concentrated and re-dissolved in $CHCl_3$. Organics are washed, dried, concentrated, and purified to yield 18-[(Amino-alkylcabamoyl)-alkylcarbonyloxy]-18-β-glycyrrhetic acid 2-trimethylsilanyl-ethyl ester. The product is stirred with a detectable marker functionalized with isothiocyanate and triethylamine in THF with DMF. The reaction mixture is then concentrated and the residue stirred in 25% TFA/$CH_2Cl_2$. The reaction mixture is concentrated and purified to yield the labeled 18-(thioureido-alkylcabamoyl-alkylcarbonyloxy)-18-β-glycyrrhetic acid.

Probes according to the present invention wherein X is a single bond and Y is O may optionally be synthesized according to the following general reaction Scheme II:

Scheme II

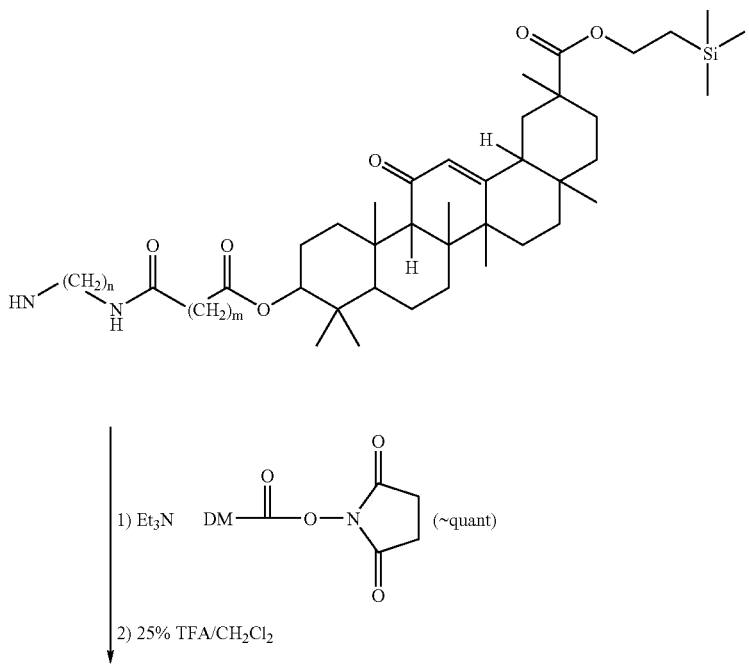

-continued

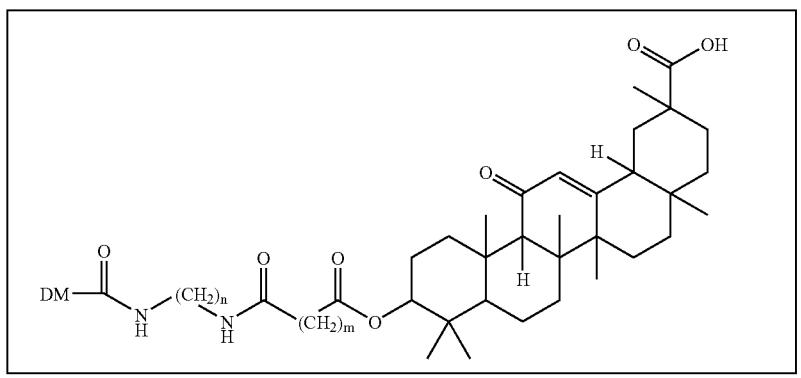

wherein m is ≧2, and preferably 2 or 3; n is ≧2, and preferably 2, 3, 4, 5, or 6; and DM is a detectable marker as described herein. In brief, the 18-[(Amino-alkylcabamoyl)-alkylcarbonyloxy]-18-β-glycyrrhetic acid 2-trimethylsilanyl-ethyl ester (see Scheme I) is stirred with a detectable marker functionalized with a succinimidyl ester and triethylamine in THF with DMF. The reaction mixture is then concentrated and the residue stirred in 25% TFA/$CH_2Cl_2$. The reaction mixture is concentrated and purified to yield the labeled 18-(carbonyl-alkylcabamoyl-alkylcarbonyloxy)-18-β-glycyrrhetic acid.

Detailed descriptions of the syntheses of particular probes according to the present invention based on the above reaction scheme are set forth in the examples.

The starting materials and reagents used in preparing probes of the present invention are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's *Reagents for Organic Synthesis*, vols. 1–17, John Wiley and Sons, New York, N.Y., 1991; *Rodd's Chemistry of Carbon Compounds*, vols. 1–5 and supps., Elsevier Science Publishers, 1989; Organic Reactions, vols. 1–40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

2. Methods Involving Use of the Probes

As noted above, probes of the present invention can be used in various methods to detect the presence of a target protein and to identify test compounds that bind to a target protein.

For example, a method may be performed comprising contacting a probe according to the present invention with a target protein to which the probe is capable of binding; and detecting the probe. This method may be used, for example, to detect a target protein in a sample and may also be used to quantify an amount of target protein in a sample.

A method may also be performed comprising: contacting a target protein with one or more test compounds in the presence of a probe according to the present invention; and detecting the probe. It is noted that the test compounds may be added to a sample comprising the target protein before, after or at the same time as the test protein and/or the probe, depending on the design of the assay.

The target protein, probe, and test compound(s) may be contacted in a variety of conventional ways depending on the particular design and purpose of the method. For example, the target protein may be contacted with the probe and/or test compound(s) by forming an assay mixture comprising the target protein and the probe and/or test compound(s). The assay mixture can also include a variety of other reagents, such as salts, buffers, neutral proteins (e.g., albumin), detergents, and the like, which may be used to facilitate optimal binding and/or reduce non-specific or background interactions. The components of the assay mixture can be added in any order that provides for the requisite bindings between the components.

The assay mixture may be incubated under conditions where the probe and/or test compound(s) selectively bind to the test protein. Incubations may be performed at any temperature that facilitates optimal binding, typically between 4° C. and 40° C., more commonly between 15° C. and 40° C. Incubation periods may likewise be selected for optimal binding but also reduced to facilitate rapid, high-throughput screening. Incubation periods are typically less than 10 hours, less than 5 hours, or less than 2 hours. For high throughput applications, it is desirable to have shorter incubation periods. In one variation, the probe with the target protein is incubated for between 0.1 and 4 hours, optionally between 0.5 and 1.5 hours.

Depending on the design of the assay, one or more separation steps may be performed to separate bound from unbound components. The separation step may be accomplished in a variety of ways. For example, one of the components (i.e., the target protein or the probe) can be immobilized on a solid substrate. Immobilization can occur before, during, or after the incubation period.

Solid supports suitable for use in the binding assays of the invention are known to those of skill in the art. Exemplar solid supports include glasses, plastics, polymers, metals, metalloids, ceramics, organics, etc. Solid supports can be flat or planar, or can have substantially different conformations. For example, the substrate can exist as particles, beads, strands, precipitates, gels, sheets, tubing, spheres, containers, capillaries, pads, slices, films, plates, dipsticks, slides, pins, etc. Magnetic beads or particles, such as magnetic latex beads and iron oxide particles, are examples of solid substrates that can be used in the methods of the invention.

Separation can be effected for example, by removing a bead or dipstick from a reservoir, emptying or diluting a reservoir such as a microtiter plate well, rinsing a bead (e.g., beads with iron cores may be readily isolated and washed using magnets), particle, chromatographic column or filter with a wash solution or solvent. The separation step may also include an extended rinse or wash, or a plurality of rinses or washes. For example, where the solid substrate is a microtiter plate, the wells may be washed several times with a washing solution, which typically includes those components of the incubation mixture that do not participate in specific binding such as salts, buffer, detergent, nonspecific protein, etc.

The assay component to be immobilized (typically the probe or the target protein) can include a tag that mediates binding of the component to the solid support. The tag can be any of a variety of components. In general, a molecule that binds the tag (a tag binder) is fixed to a solid support, and the tagged protein or probe is attached to the solid support by interaction of the tag and the tag binder. A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Similarly, any haptenic or antigenic compound can be used in combination with an appropriate antibody to form a tag/tag binder pair. Many other tag/tag binder pairs are also useful in assay systems described herein, as would be apparent to one of skill in the art upon review of this disclosure. Specific tag—tag binder interactions occur when the tag and tag binder bind with a $K_D$ of at least about 0.01 µM, at least about 0.001 µM or better, or at least about 0.0001 µM or better, under standard assay conditions.

Methods for attaching tags to proteins are known to those of skill in the art. In one embodiment, preparation of a tagged assay component involves producing a fusion protein by recombinant methods. For example, a polynucleotide encoding the target protein is operably linked to a polynucleotide that encodes an epitope for which convenient means of detection exist. The polynucleotide encoding the epitope is preferably placed at a location relative to the protein coding sequence that does not disrupt the ability of the fusion protein to bind to its corresponding target. Methods for constructing and expressing genes that encode fusion proteins are well known to those of skill in the art.

Tag binders may be fixed to solid substrates using any of a variety of methods known to those skilled in the art. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion include amine, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature (e.g., Merrifield, *J. Am. Chem. Soc.* 85: 2149–2154 (1963); Geysen et al., *J. Immun. Meth.* 102: 259–274 (1987); Frank et al., *Tetrahedron* 44: 6031–6040 (1988); Fodor et al., *Science* 251: 767–777 (1991); Sheldon et al., *Clinical Chemistry* 39(4): 718–719 (1993); Kozal et al., *Nature Medicine* 2(7): 753–759 (1996)). Non-chemical approaches for fixing tag binders to substrates include other common methods, such as heat, cross-linking by UV radiation, and the like.

Detection of the probe is achieved by detection of the detectable marker (DM) attached to the probe. In some instances, the probe is designed and detection is performed such that it is possible to differentiate the probe complexed to the target protein from free, unbound probe. This is advantageous in regard to reducing the need to immobilize the probe and/or target protein and allows the method to be conducted in solution.

Detection of the probe may be effectuated in any manner convenient for quantifying the detectable marker. Non-radioactive detection methods have become increasingly widespread because of the costs associated with radiolabeled reagents and their disposal. Fluorescence spectroscopy is one of the most prevalent non-radioactive detection methods.

One particular method for detecting probes is via fluorescence polarization. Fluorescence polarization is independent of total fluorescence intensity but is dependent on the rate at which the fluorescent molecule tumbles in solution. As a result, fluorescence polarization allows one to differentiate between bound and unbound probe in solution without any isolation steps.

In general, any instrument capable of monitoring a particular detectable marker can be used to detect the detectable marker. Typical detection instruments include spectrophotometers, phototubes and photodiodes, microscopes, scintillation counters, cameras, film and the like, as well as combinations thereof, each of which are widely available from a variety of commercial sources known to persons of skill in the art. An optical image of a substrate comprising bound labeling moieties optionally is digitized for subsequent computer analysis.

Test compounds that are identified as modulators of a target protein according to the methods of the present invention may serve as lead compounds for drug development. Ultimately, such lead compounds may be refined as drugs for a variety of conditions, including metabolic syndromes (e.g., diabetes and obesity), Cushing's disease, hypertension, cognitive function (e.g., dementia), ocular function (e.g., intraocular pressure), and osteoporosis. Accordingly, the methods of the present invention are of immediate value for their ability to identify lead compounds for pharmaceutical or other applications.

Essentially any chemical entity can be evaluated as a test compound using the methods of the present invention. Further, the methods of the present invention are well adapted for automation and high-throughput screening ("HTS"), particularly because the methods may be conducted without use of radioactive reagents or gel separation steps. It is noted that the methods of the present invention may be adapted to screen large chemical libraries by automating one or more steps of the method. In addition, the methods may be run in parallel (e.g., in microtiter formats on microtiter plates in robotic assays).

In one particular embodiment, the methods of the present invention are used to screen a library of test compounds to identify those library members that appear to compete with the probe for binding to the target protein. Selected members of the library identified through the screen may serve as conventional "lead compounds" for the further development of drugs against the target protein.

Preparation and screening of chemical libraries is well known to those of skill in the art. Such chemical libraries include, but are not limited to, peptide libraries (see, e.g., U.S. Pat. No. 5,010,175; Furka, *Int. J. Pept. Prot. Res.* 37:487–493 (1991); Houghton et al., *Nature* 354:84–88 (1991)). Other chemistries for generating chemically diverse libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with β-D-glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries, peptide nucleic acid libraries (see, e.g., U.S. Pat. No. 5,539,083), antibody libraries (see, e.g., Vaughn et al., *Nature Biotechnology* 14(3):309–314 (1996) and PCT/US96/10287), carbohydrate libraries (see, e.g., Liang et al., *Science* 274:1520–1522 (1996) and U.S. Pat. No. 5,593,853), small organic molecule libraries (see, e.g., benzodiazepines, Baum, *C&E News* Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of chemical libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous chemical libraries are themselves commercially available (see, e.g., ComGenex, Princeton, N. J.; Asinex, Moscow, Ru; Tripos, Inc., St. Louis, Mo.; ChemStar, Ltd, Moscow, RU; 3D Pharmaceuticals, Exton, Pa.; Martek Biosciences, Columbia, Md.; etc.).

Control reactions that measure the affinity of the probe for the target protein in the absence of test compounds are optionally performed to provide background levels of binding activity. Such optional control reactions can increase the reliability of the methods of the present invention. In some instances, it is also desirable to have positive controls to ensure that the method is being conducted accurately.

3. 11β-Hydroxysteroid Dehydrogenase Type 1 (HSD11B1)

The probes of the present invention are particularly suited for the detection of HSD11B1 and for identifying potential modulators of HSD11B1. HSD11B1 belongs to the short chain dehydrogenase subfamily. As such, it is expected that the probes of the present invention may also be useful with other structurally similar proteins, such as various other members of the short chain dehydrogenase subfamily. Accordingly, it is intended that the probes and methods of the present invention extend not only to HSD11B1 but also to any target protein to which the probe is capable of binding.

HSD11B1 comprises the wild-type form of full length HSD11B1, set forth herein as SEQ. ID No. 1 (GenBank Accession Number NM_005525; Tannin et al., *J. Biol. Chem.* 266 (25), 16653–16658(1991)). In addition, HSD11B1 comprises fragments of the full length HSD11B1. For example, HSD11B1 includes fragments comprising residues 24–292 of SEQ. ID No. 1, which comprise the active site domain of wild-type HSD11B1.

It should be recognized that the invention can be readily extended to various variants, isoforms, mutants, analogs, fusion proteins, and fragments of wild-type HSD11B1. For example, HSD11B1 variants comprising a sequence that has about 55%, about 65%, about 75%, about 85%, about 90%, about 95%, about 97%, about 99% or greater identity with SEQ. ID No. 1 are expected to be useful with the assays, methods, and probes of the present invention.

Variants of HSD11B1 may be insertional variants in which one or more amino acid residues are introduced into a predetermined site in the HSD11B1 sequence. For instance, insertional variants can be fusions of heterologous proteins or polypeptides to the amino or carboxyl terminus of the subunits.

Variants of HSD11B1 may also be substitutional variants in which at least one residue has been removed and a different residue inserted in its place. Non-natural amino acids (i.e., amino acids not normally found in native proteins), as well as isosteric analogs (amino acid or otherwise) may optionally be employed in substitutional variants. Examples of suitable substitutions are well known in the art, such as Glu→Asp, Asp→Glu, Ser→Cys, and Cys→Ser, for example.

Another class of variants is deletional variants, which are characterized by the removal of one or more amino acid residues from the HSD11B1 sequence.

Other variants may be produced by chemically modifying amino acids of the native protein (e.g., diethylpyrocarbonate treatment that modifies histidine residues). Preferred are chemical modifications that are specific for certain amino acid side chains. Specificity may also be achieved by blocking other side chains with antibodies directed to the side chains to be protected. Chemical modification includes such reactions as oxidation, reduction, amidation, deamidation, or substitution of bulky groups such as polysaccharides or polyethylene glycol.

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; O-methylisourea, 2,4-pentanedione; and transaminase catalyzed reaction with glyoxylate, and N-hydroxysuccinamide esters of polyethylene glycol or other bulky substitutions.

Arginyl residues may be modified by reaction with a number of reagents, including phenylglyoxal, 2,3-butanedione, 1,2-cyclohexanedione, and ninhydrin. Modification of arginine residues requires that the reaction be performed in alkaline conditions because of the high $pK_a$ of the guanidine functional group. Furthermore, these reagents may react with the groups of lysine as well as the arginine epsilon-amino group.

Tyrosyl residues may also be modified to introduce spectral labels into tyrosyl residues by reaction with aromatic diazonium compounds or tetranitromethane, forming 0-acetyl tyrosyl species and 3-nitro derivatives, respectively. Tyrosyl residues may also be iodinated using $^{125}I$, or $^{131}I$ to prepare labeled proteins for use in radioimmunoassays.

Carboxyl side groups (aspartyl or glutamyl) may be selectively modified by reaction with carbodiimides or they may be converted to asparaginyl and glutaminyl residues by reaction with ammonium ions. Conversely, asparaginyl and glutaminyl residues may be deamidated to the corresponding aspartyl or glutamyl residues, respectively, under mildly acidic conditions. Either form of these residues falls within the scope of this invention.

Other modifications that may be formed include the hydroxylation of proline and lysine, phosphorylation of hydroxyl groups of seryl or threonyl groups of lysine, arginine and histidine side chains (T. E. Creighton, *Proteins:*

*Structure and Molecular Properties*, W.H. Freeman & Co., San Francisco, pp. 79–86, 1983), acetylation of the N-terminal amine and amidation of any C-terminal carboxyl group.

An example of a fusion protein is provided by SEQ. ID No.2, which includes a 6 residue N-terminal tag (6 residues are histidine) and a rTev cleavage site that may be used to facilitate purification of the protein.

As will be appreciated by those skilled in the art, modifications of the nucleic sequence encoding HSD11B1 may be accomplished by a variety of well-known techniques, such as site-directed mutagenesis (see, Gillman et al., *Gene* 8:81–97 (1979); Roberts et al., *Nature* 328:731–734 (1987)). When modifications are made, these modifications may optionally be evaluated for there affect on a variety of different properties including, for example, solubility, crystallizability and a modification to the protein's structure and activity.

In one variation, the variant and/or fragment of wild-type HSD11B1 is functional in the sense that the resulting protein is capable of associating with at least one same chemical entity that is also capable of selectively associating with a protein comprising the wild-type HSD11B1 (e.g., residues 24–292 of SEQ. ID No. 1) since this common associative ability evidences that at least a portion of the native structure has been conserved.

Amino acid substitutions, deletions and additions that do not significantly interfere with the activity of HSD11B1 will depend, in part, on the region where the substitution, addition or deletion occurs in the crystal structure. In highly variable regions of the molecule, non-conservative substitutions as well as conservative substitutions, may be tolerated without significantly disrupting the activity of the molecule. In highly conserved regions, or regions containing significant secondary structure, conservative amino acid substitutions are preferred.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. Other conservative amino acid substitutions are well known in the art.

It will be understood that the protein may be produced in whole or in part by chemical synthesis. As a result, the selection of amino acids available for substitution or addition is not limited to the genetically encoded amino acids. Indeed, mutants may optionally contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues in order to provide convenient cloning sites in cDNA encoding the polypeptide, to aid in purification of the polypeptide, etc. Such substitutions, deletions and/or additions which do not substantially alter the three dimensional structure of HSD11B1 will be apparent to those having skills in the art, particularly in view of the three dimensional structure of HSD11B1 provided herein.

The gene encoding HSD11B1 can be isolated from RNA, cDNA or cDNA libraries. In this case, the portion of the gene encoding amino acid residues 24–292 (SEQ. ID No. 1), which comprises the active site of wild-type HSD11B1, was isolated and is shown as SEQ. ID No. 3.

Construction of expression vectors and recombinant proteins from the DNA sequence encoding HSD11B1 may be performed by various methods well known in the art. For example, these techniques may be performed according to Sambrook et al., Molecular Cloning—A Laboratory Manual, Cold Spring Harbor, N.Y. (1989), and Kriegler, M., Gene Transfer and Expression, A Laboratory Manual, Stockton Press, New York (1990).

A variety of expression systems and hosts may be used for the expression of HSD11B1. Example 1 provides one such expression system.

Once expressed, purification steps are employed to produce HSD11B1 in a relatively homogeneous state. In general, a higher purity solution of a protein increases the likelihood that the protein will crystallize. Typical purification methods include the use of centrifugation, partial fractionation, using salt or organic compounds, dialysis, conventional column chromatography, (such as ion exchange, molecular sizing chromatography, etc.), high performance liquid chromatography (HPLC), and gel electrophoresis methods (see, e.g., Deutcher, "Guide to Protein Purification" in Methods in Enzymology (1990), Academic Press, Berkeley, Calif.).

HSD11B1 may optionally be affinity labeled during cloning, preferably with a N-terminal six-histidine tag and rTev cleavage site, in order to facilitate purification. With the use of an affinity label, it is possible to perform a one-step purification process on a purification column that has a unique affinity for the label. The affinity label may be optionally removed after purification. These and other purification methods are known and will be apparent to one of skill in the art.

4. Compositions, Kits, and Integrated Systems

The present invention provides compositions incorporating the probes of the present invention which may be used, among other things, for practicing the methods of the present invention. In one embodiment, a composition is provided comprising a probe according to the present invention and a target protein, particularly HSD11B1. The composition may be a powder ready for reconstitution and use in an assay. Alternatively, the composition may be an aqueous solution comprising the probe and the target protein. In another embodiment, a composition is provided comprising a probe according to the present invention attached to a solid support. In each case, the compositions can include additional reagents such as salts, buffers and other additives that do not deleteriously affect the utility of the probes for performing the methods of the present invention. Each of the compositions may be incorporated into a kit, as described herein.

The present invention also provides kits incorporating the probes of the present invention which may be used, among other things, for practicing the methods of the present invention.

In one embodiment, a kit is provided that comprises a probe according to the present invention. The kit may optionally also include a protein to which the probe is capable of binding. In one variation, the protein is 11β-hydroxysteroid dehydrogenase. The kit may also include one or more known protein modulators that may be used as a standard in conjunction with the probe. Within the kit, the probe, protein, and/or protein modulator(s) may each independently be (a) in purified form; (b) attached to a solid support; and/or (c) in solution, depending on the design of assay for which the kit is designed.

The kit may also comprise instructions for using the probe or for storing the probe and kit. The kit may also comprise packaging materials for housing one or more compositions comprising the probe, protein, and/or protein modulator(s). Examples of packaging materials include, but are not limited to containers or compartments that are used to house the probe, protein, and/or protein modulator(s). The packaging materials may include written information including instructions regarding the probe and the kit. Other elements typically incorporated in kits used in biological assays may also be included.

The invention also provides integrated systems for high-throughput screening of test compounds. The system may include a robotic armature which transfers fluid from a source to a destination, a controller which controls the robotic armature, a label detector, a data storage unit which records label detection, and an assay component such as a microtiter dish comprising a well having a reaction mixture or a substrate comprising a fixed nucleic acid or immobilization moiety.

A number of robotic fluid transfer systems are available. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous STAT binding assays.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip-compatible DOS™, OS2™, WINDOWS™, WINDOWS NT™ or WINDOWS95™ based computers), MACINTOSH™, or UNIX based (e.g., SUN™ work station) computers.

One conventional system carries light from the specimen field to a cooled charge-coupled device (CCD) camera. The CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

EXAMPLES

Various methods may be developed for synthesizing probes according to the present invention. Representative methods for synthesizing these probes are provided in the Examples. It is noted, however, that the probes of the present invention may also be synthesized by other synthetic routes that others may devise.

It will be readily recognized that certain probes according to the present invention have atoms with linkages to other atoms that confer a particular stereochemistry to the probe (e.g., chiral centers). It is recognized that synthesis of compounds according to the present invention may result in the creation of mixtures of different stereoisomers (enantiomers, diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) that they can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Example 1

Expression and Purification of HSD11B1

This example describes cloning, expression and purification of HSD11B1. It should be noted that a variety of other expression systems and hosts are also suitable for the expression of HSD11B1, as would be readily appreciated by one of skill in the art.

Residues 24 to 292 of 11-β-hydroxysteroid dehydrogenase isoform 1 was amplified from IMAGE clone 5193867 (ATCC clone 7277078) using PCR with the primers hsd1_24-f: 5'-AACGAGGAATTCAGACCAGAGATG-3' (SEQ. ID No. 4) and hsd1-292-r: 5'-TTACTTGTTTATGAATCT-GTCCAT-3' (SEQ. ID No. 5). The resulting PCR product was topocloned into the pBAD-ThioE vector (Invitrogen) that was modified by inserting a DNA sequence that codes for MKHQHQHQHQHQHQQPL at the cloning site and adapted for TOPOcloning PCR (Invitrogen). Residues 24–292 of 11-β-hydroxysteroid dehydrogenase isoform 1 were generated fused with MKHQHQHQHQHQHQQPL at the N-terminus under control of an ara promoter. One point mutation C272S was made in the final construct by quick change PCR mutagenesis using the primers hsdC272Sqcf: 5'-TCAGAAATCCATCCAGGAAGATC-3' (SEQ. ID No. 6) and hsdC272Sqcr: 5'-GATCTTCCTGGATG-GATTTCTGA-3' (SEQ. ID No. 7).

E. coli DH10b-Tir (Invitrogen), harboring the HSD11B1 expression plasmid, were grown overnight at 37° C., in Luria broth (LB) supplemented to 0.05 mg/ml kanamycin (Km). 15 mls of saturated culture was then used to inoculate one liter of fresh LB (0.05 mg/ml Km). When this culture reached an optical density of 0.4 (λ=600 nm), the growth temperature was shifted from 37° C. to 25° C. After an additional 2 hours of growth, arabinose and corticosterone were added to a final concentration of 0.2% (w/w), and 0.25 mM, respectively. Cells were harvested approximately 14 hours following induction, and were immediately frozen at −80° C. The cell pellets from each liter of cell culture were thawed and resuspended in 50 mls of lysis buffer (30 mM CHAPS, 50 mM Tris-HCl, pH 7.9, 0.15 M NaCl, 0.5 µl/ml benzonase, 1 µl/ml ReadyLyse). Following a 30-minute incubation at room temperature, the lysates were clarified by centrifugation. The resulting supernatant was loaded on 6 mls of Probond resin (Invitrogen), previously equilibrated with wash buffer (4 mM CHAPS, 50 mM Tris-HCl, pH 7.9, 0.25 M NaCl, 40 mM imidazole), and then washed with 10 column volumes of wash buffer. HSD11B1 was then eluted with 3 column volumes of wash buffer supplemented to 0.2 M imidazole. The eluate of purified HSD11B1 was extensively dialysed against 4 mM CHAPS, 25 mM Tris-HCl, pH 7.9, 0.25 M NaCl, and concentrated to 10 mg/ml. Size exclusion chromatography demonstrated that this method of purification yields monodispersive HSD11B1.

Example 2A

18-β-Glycyrrhetic acid 2-trimethylsilanyl-ethyl ester

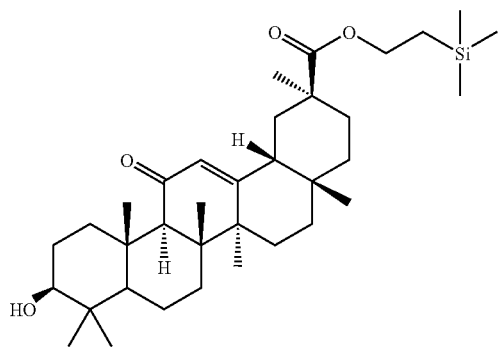

2-(Trimethylsilyl)ethanol (0.86 mL, 6.0 mmol) and 2-chloro-1,3-dimethylimidazolinium chloride (0.85 g, 5.4 mmol) were added to a solution of 18-β-glycyrrhetic acid (1.26 g, 2.7 mmol) in pyridine (8 mL). After stirring for 16 h at r.t., the solution was poured over water and extracted with CH$_2$Cl$_2$. Organics were washed with 1N HCl and brine, dried (MgSO$_4$), and concentrated in vacuo. Purification by silica gel chromatography (20% EtOAc/hexanes) gave 1.24 g (81%) of the title compound as a white solid. $^1$H NMR (400 MHz, CDCl$_3$): δ 5.66 (s, 1H), 4.11–4.23 (m, 2H), 3.20–3.26 (m, 1H), 2.76–2.82 (m, 1H), 2.34 (s, 1H), 0.68–2.14 (m, 42H), 0.05 (s, 9H). MS (ES) [m+H] calculated for C$_{35}$H$_{58}$O$_4$Si 571; found 571.

Example 2B 18-(3-Carboxypropionyloxy)-18-β-glycyrrhetic acid 2-trimethylsilanyl-ethyl ester

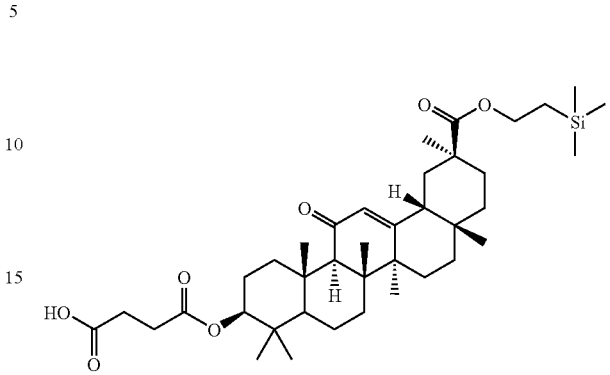

Example 2A (660 mg, 1.16 mmol) and succinic anhydride (463 mg, 4.63 mmol) were combined in pyridine (8 mL) with triethylamine (2 mL) in a sealed tube, and the solution was heated at 116° C. for 18 h. The reaction was cooled and concentrated in vacuo. The residue was diluted with acetone (5 mL) and ice water (15 mL), then adjusted to pH=3 with 1N HCl. The solution was extracted with EtOAc. Organics were dried (MgSO$_4$) and concentrated. Purification by silica gel chromatography (30% to 100% EtOAc/hexanes) gave 648 mg (83%) of the title compound as a white solid. $^1$H NMR (400 MHz, CDCl$_3$): δ 5.65 (s, 1H), 4.50–4.56 (m, 1H), 4.10–4.21 (m, 2H), 2.75–2.82 (m, 1H), 2.60–2.70 (m, 4H), 2.36 (s, 1H), 0.78–2.16 (m, 42H), 0.05 (s, 9H). MS (ES) [m+H] calculated for C$_{39}$H$_{62}$O$_7$Si 671; found 671.

Example 2C

18-[3-(2-Amino-ethylcabamoyl)-propionyloxy]-18-β-glycyrrhetic acid 2-trimethylsilanyl-ethyl ester

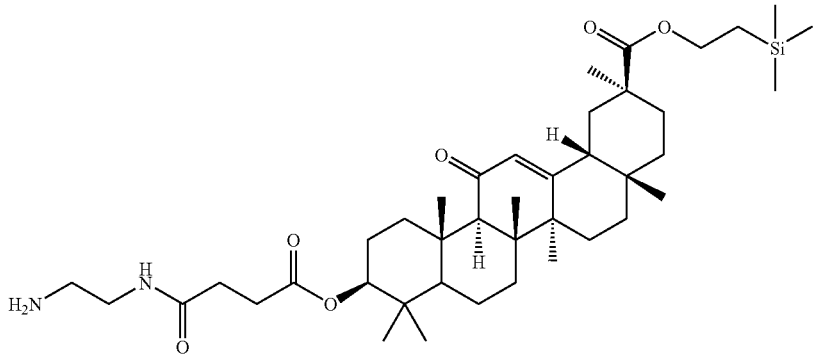

Example 2B (256 mg, 0.383 mmol) and ethylenediamine (256 μL, 3.83 mmol) were stirred in DMF (5 mL) at r.t. PyBOP (399 mg, 0.766 mmol) and triethylamine (107 μL, 0.766 mmol) were added, and the reaction stirred 18 h. The solution was concentrated and re-dissolved in CHCl$_3$. Organics were washed with sat. NaHCO$_3$ and brine, dried (MgSO$_4$), and concentrated. Purification by silica gel chromatography gave 247 mg (90%) of the title compound as a white solid. $^1$H NMR (400 MHz, CDCl$_3$): δ 6.98 (br s, 1H), 6.82 (br s, 2H), 5.64 (s, 1H), 4.49–4.54 (m, 1H), 4.10–4.21

(m, 2H), 3.20–3.60 (m, 6H), 2.71–2.77 (m, 1H), 2.52–2.66 (m, 2H), 2.39 (s, 1H), 0.77–2.16 (m, 42H), 0.05 (s, 9H). MS (ES) [m+H] calculated for $C_{41}H_{68}N_2O_6Si$ 713; found 713.

Example 2

18-{3-[2-(5'-Fluoresceinyl)-thioureido-ethylcabamoyl]-propionyloxy}-18-β-glycyrrhetic acid

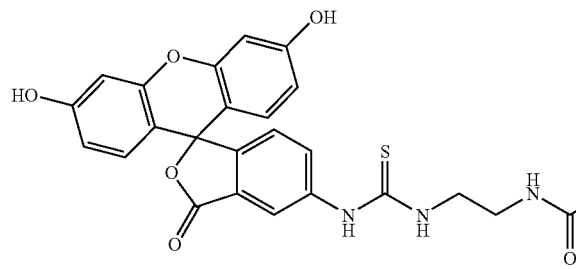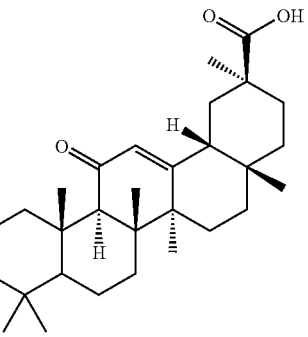

Example 2C (240 mg, 0.34 mmol), fluorescein isothiocyanate, isomer I (131 mg, 0.34 mmol), and triethylamine (47 μL, 0.34 mmol) were stirred in THF (5 mL) with DMF (1 mL) at r.t. for 1 h. The reaction was concentrated in vacuo, and the residue stirred in 25% TFA/CH$_2$Cl$_2$ (5 mL) for 16 h. The reaction was concentrated and purified by Prep-HPLC to give 155.8 mg (46%) of the title compound as an orange solid. $^1$H NMR (400 MHz, DMSO-d$_6$): δ 12.20 (br s, 1H), 10.12 (br s, 2H), 10.03 (s, 1H), 8.15 (s, 1H), 8.08 (s, 2H), 7.70 (s, 1H), 7.17 (d, 1H, J=8.0 Hz), 6.66 (d, 2H, J=1.6 Hz), 6.52–6.60 (m, 4H), 5.75 (s, 1H), 5.39 (s, 1H), 4.37–4.42 (m, 1H), 3.51–3.59 (m, 2H), 3.22–3.29 (m, 2H), 0.72–2.61 (m, 45H). MS (ES) [m+H] calculated for $C_{57}H_{67}N_3O_{11}S$ 1002; found 1002.

Example 3

Method for Screening Protein Modulators of 11β-hydroxysteroid dehydrogenase using 18-{3-[2-(5'-Fluoresceinyl)-thioureido-ethylcabamoyl]-propionyloxy}-18-β-glycyrrhetic acid The binding properties of test compounds relative to 11-β-HSD1 may be determined by competitive fluorescence polarization (FP) detection using a Greiner small volume black 384-well-plate format under the following reaction conditions: 50 mM Hepes pH 7.5, 150 mM NaCl, 0.01% Brij35, 100 nM 11-β-HSD1, 2% DMSO, and 10 nM of the probe. Bound and unbound probe concentration may be determined quantitatively by FP detection using an Analyst HT plate reader (Molecular Devices) with an excitation wavelength of 485 nm and an emission wavelength of 530 nm, and using a Fluorescein 505 dichroic mirror.

The binding assay may be initiated as follows: diluted enzyme is incubated for 30 minutes at room temperature, then 8 μl of (2.5×) 250 nM 11-β-HSD1 enzyme is added to the wells of the plate, followed by the addition of 4 μl of (5×) test compound (2 fold serial dilutions for 11 data points for each test compound) containing 10% DMSO. The reaction mixture is then incubated at room temperature for 10 min. 8 μl of (2.5×) 25 nM probe compound is then added to the wells. Fluorescence polarization readings of the resulting reaction mixtures are measured after a 60-minute incubation at room temperature. EC50 values can be calculated by non-linear curve fitting of the compound concentrations and fluorescent polarization values.

While the present invention is disclosed with reference to certain embodiments and examples detailed above, it is understood that the embodiments and examples described herein are for illustrative purposes only and that various modifications or changes in light thereof will be apparent to those skilled in the art and are to be included within the spirit and scope of this application and the appended claims. All patents, patent applications, papers, publications, and books cited in this application are incorporated by reference herein in their entirety for all purposes.

---

What is claimed is:

1. A probe comprising:

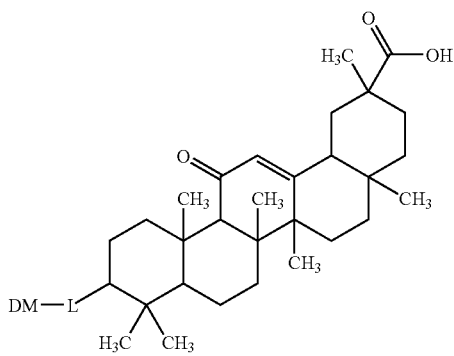

wherein

DM is a detectable marker; and

L is a straight or branched chain moiety providing between 1 and 20 atom separation between DM and the ring atom to which DM is attached.

2. A probe according to claim 1 wherein L comprises the formula:

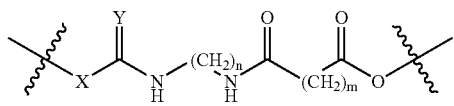

wherein:

X is selected from the group consisting of NH and a single bond;

Y is selected from the group consisting of S or O;

m is ≧2; and n is ≧2.

3. A probe according to claim 2 wherein DM is a fluorescent detectable marker.

4. A probe according to claim 2 wherein DM comprises the formula

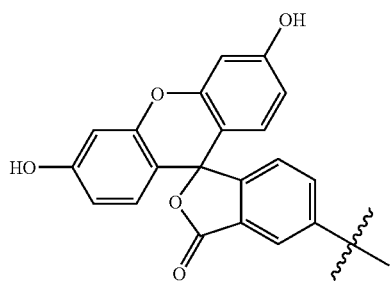

5. A probe according to claim 1 wherein L comprises the formula:

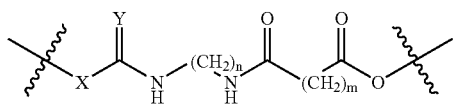

wherein:

X is selected from the group consisting of NH and a single bond;

Y is selected from the group consisting of S or O;

m is 2 or 3; and n is 2, 3, 4, 5, or 6.

6. A probe according to claim 5 wherein DM is a fluorescent detectable marker.

7. A probe according to claim 5 wherein DM comprises the formula

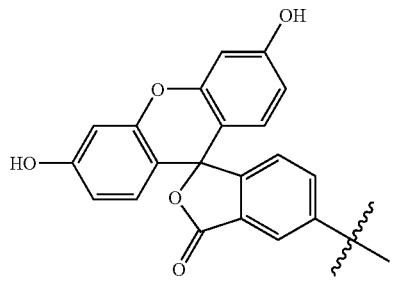

8. A probe according to claim 1 wherein DM is a detectable marker selected from the group consisting of photoreactive groups; fluorescent labels; chemiluminescent labels; colorimeteric labels; enzymatic markers; radioactive isotopes; biotin-streptavidin; digoxigenin haptens; and electron-dense reagents.

9. A probe according to claim 1 wherein DM is a fluorescent detectable marker.

10. A probe according to claim 1 wherein DM comprises the formula:

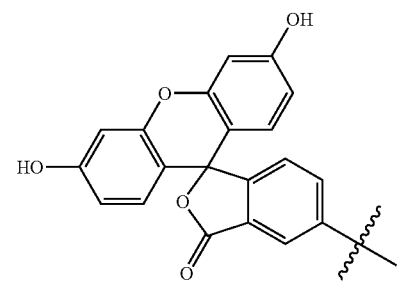

and wherein the probe is attached to a solid support.

11. A probe comprising:

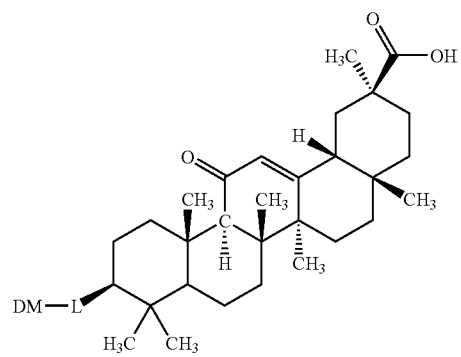

wherein

DM is a detectable marker; and

L is a straight or branched chain moiety providing between 1 and 20 atom separation between DM and the ring atom to which DM is attached.

12. A probe according to claim 11 wherein L comprises the formula:

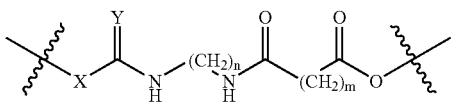

wherein:

X is selected from the group consisting of NH and a single bond;

Y is selected from the group consisting of S or O;

m is $\geq 2$; and n is $\geq 2$.

13. A probe according to claim 12 wherein DM is a fluorescent detectable marker.

14. A probe according to claim 12 wherein DM comprises the formula:

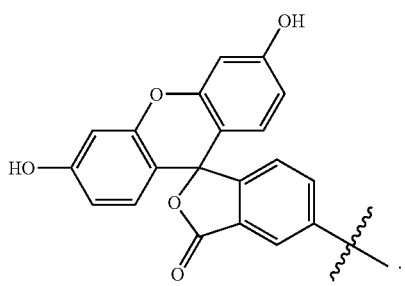

15. A probe according to claim 11 wherein L comprises the formula:

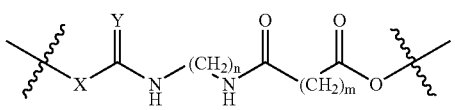

wherein:

X is selected from the group consisting of NH and a single bond;

Y is selected from the group consisting of S or O;

m is 2 or 3; and n is 2, 3, 4, 5, or 6.

16. A probe according to claim 15 wherein DM is a fluorescent detectable marker.

17. A probe according to claim 15 wherein DM comprises the formula:

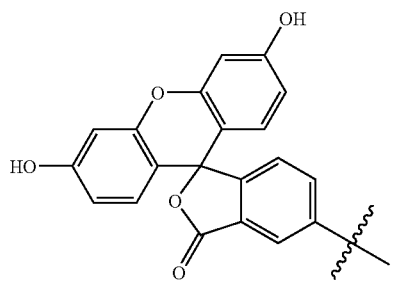

18. A probe according to claim 11 wherein DM is a detectable marker selected from the group consisting of photoreactive groups; fluorescent labels; chemiluminescent labels; colorimeteric labels; enzymatic markers; radioactive isotopes; biotin-streptavidin; digoxigenin haptens; and electron-dense reagents.

19. A probe according to claim 11 wherein DM is a fluorescent detectable marker.

20. A probe according to claim 11 wherein DM comprises the formula:

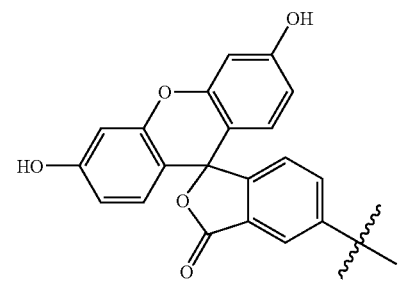

and wherein the probe is attached to a solid support.

21. A composition comprising:

a probe immobilized on a solid support where the probe comprises the formula:

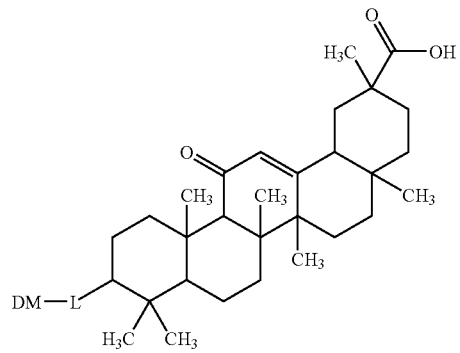

wherein

DM is a detectable marker; and

L is a straight or branched chain moiety providing between 1 and 20 atom separation between DM and the ring atom to which DM is attached.

22. A method comprising:
contacting a probe with a target protein to which the probe is capable of binding; and
detecting the probe;
wherein the probe comprises the formula:

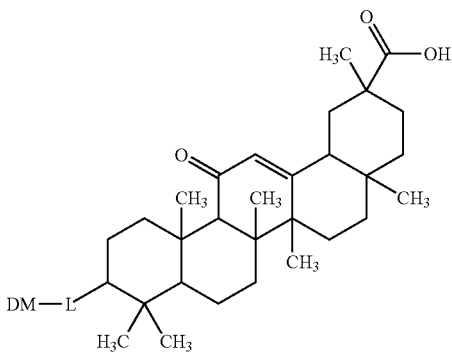

wherein
DM is a detectable marker; and
L is a straight or branched chain moiety providing between 1 and 20 atom separation between DM and the ring atom to which DM is attached.

23. A method according to claim 22 wherein detecting the probe comprises detecting a probe—target protein complex.

24. A method according to claim 22 wherein detecting the probe is performed without having to perform a separate step to remove probe that is not bound to the target protein.

25. A method according to claim 22 wherein detecting the probe is performed with the probe and the target protein both in solution.

26. A method according to claim 22 wherein the detectable marker is a fluorescent label.

27. A method according to claim 22 wherein detecting the probe is performed by fluorescence polarization.

28. A method according to claim 22 wherein the target protein is attached to a solid support.

29. A method according to claim 22 wherein the target protein is 11β-hydroxysteroid dehydrogenase.

30. A method comprising:
contacting a target protein with one or more test compounds in the presence of a probe; and
detecting the probe;
wherein the probe comprises the formula:

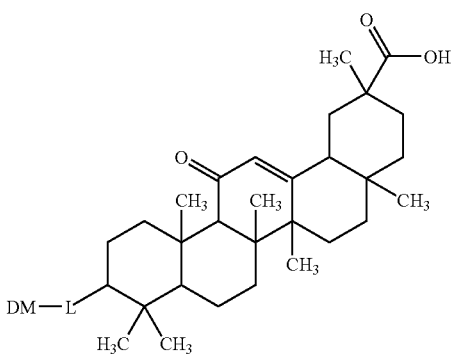

wherein
DM is a detectable marker; and
L is a straight or branched chain moiety providing between 1 and 20 atom separation between DM and the ring atom to which DM is attached.

31. A method according to claim 30 wherein detecting the probe comprises detecting a probe—target protein complex.

32. A method according to claim 30 wherein detecting the probe is performed without having to perform a separate step to remove probe that is not bound to the target protein.

33. A method according to claim 30 wherein detecting the probe is performed with the probe, target protein and test compound(s) in solution.

34. A method according to claim 30 wherein the detectable marker is a fluorescent label.

35. A method according to claim 30 wherein detecting the probe is performed by fluorescence polarization.

36. A method according to claim 30 wherein the target protein is 11β-hydroxysteroid dehydrogenase.

37. A method according to claim 30 wherein the method is conducted in a high throughput format.

38. A method according to claim 30 wherein the method is conducted in a multiwell plate.

39. A method according to claim 30 wherein the method further comprises determining a binding affinity of the test compound(s) for the target protein.

40. A method according to claim 30 wherein the method further comprises performing one or more control experiments where no test compounds are added and/or no target protein is added.

41. A method according to claim 30 wherein the method further comprises forming a standard curve against which results of the method from different samples may be compared.

42. A method comprising:
contacting a probe according to the present invention with a target protein to which the probe is capable of binding in the absence of test compounds;
detecting a formation of a probe—target protein complex;
adding one or more test compounds; and
detecting a change in the amount of probe—target protein complex after addition of the one or more test compounds;
wherein the probe comprises the formula:

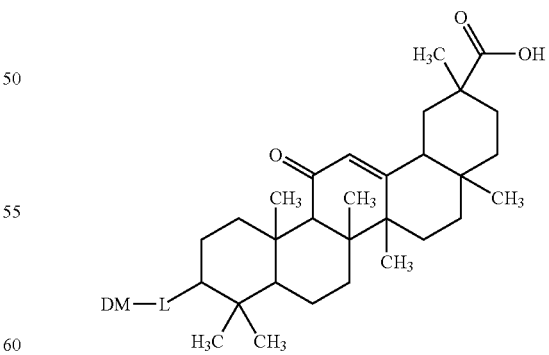

wherein
DM is a detectable marker; and
L is a straight or branched chain moiety providing between 1 and 20 atom separation between DM and the ring atom to which DM is attached.

43. A method according to claim 42 wherein detection of the probe—target protein complex and the change in the amount of probe—target protein complex after addition of the one or more test compounds is performed by fluorescence polarization.

44. A method according to claim 42 wherein detecting the formation of a probe—target protein complex comprises detecting a probe—target protein complex.

45. A method according to claim 42 wherein detecting the formation of a probe—target protein complex is performed without having to perform a separate step to remove probe that is not bound to the target protein.

46. A method according to claim 42 wherein detecting the formation of a probe—target protein complex is performed with the probe, target protein and test compound(s) in solution.

47. A method according to claim 42 wherein the detectable marker is a fluorescent label.

48. A method according to claim 42 wherein detecting the formation of a probe—target protein complex is performed by fluorescence polarization.

49. A method according to claim 42 wherein the target protein is 11β-hydroxysteroid dehydrogenase.

50. A method according to claim 42 wherein the method is conducted in a high throughput format.

51. A method according to claim 42 wherein the method is conducted in a multiwell plate.

52. A method according to claim 42 wherein the method further comprises determining a binding affinity of the test compound(s) for the target protein.

53. A method according to claim 42 wherein the method further comprises performing one or more control experiments where no test compounds are added and/or no target protein is added.

54. A method according to claim 42 wherein the method further comprises forming a standard curve against which results of the method from different samples may be compared.

55. A kit comprising:
a probe; and
a protein to which the probe is capable of binding;
wherein the probe comprises the formula:

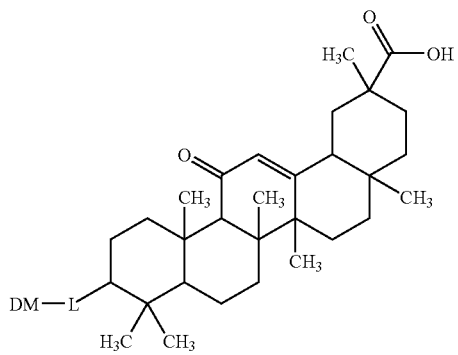

wherein
DM is a detectable marker; and
L is a straight or branched chain moiety providing between 1 and 20 atom separation between DM and the ring atom to which DM is attached.

56. A kit according to claim 55 wherein the protein is 11β-hydroxysteroid dehydrogenase.

57. A kit according to claim 55 wherein the kit comprises one or more modulators of the protein.

58. A kit according to claim 55 wherein the probe is in purified form.

59. A kit according to claim 55 wherein the probe is attached to a solid support.

60. A kit according to claim 55 wherein the protein is attached to a solid support.

61. A kit according to claim 55 wherein the probe and protein are in solution.

62. A kit comprising:
a probe; and
instructions for using the probe;
wherein the probe comprises the formula:

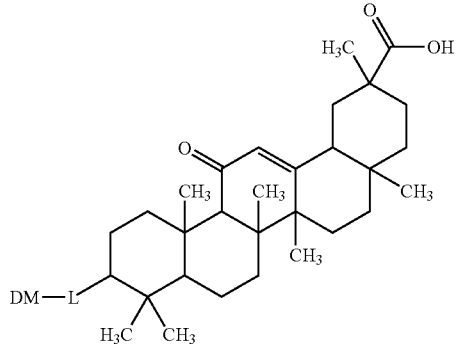

wherein
DM is a detectable marker; and
L is a straight or branched chain moiety providing between 1 and 20 atom separation between DM and the ring atom to which DM is attached.

63. A kit comprising:
a probe; and
packaging materials for housing a composition comprising the probe;
wherein the probe comprises the formula

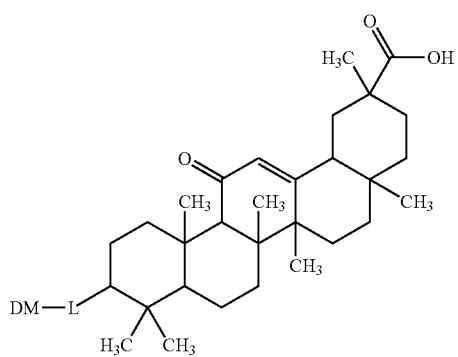

wherein
DM is a detectable marker; and
L is a straight or branched chain moiety providing between 1 and 20 atom separation between DM and the ring atom to which DM is attached.

* * * * *